(12) United States Patent
Koops et al.

(10) Patent No.: US 7,935,418 B2
(45) Date of Patent: May 3, 2011

(54) FUNCTIONAL POROUS FIBRES

(75) Inventors: Geert-Hendrik Koops, Zwolle (NL); Maria Elena Avramescu, Juelich (DE); Zandrie Borneman, Hengelo (NL); Ryotaro Kiyono, Nagano (JP); Matthias Wessling, Enschede (NL)

(73) Assignee: Mosaic Systems B.V., Breda (NL)

( * ) Notice: Subject to any disclaimer, the term of this patent is extended or adjusted under 35 U.S.C. 154(b) by 702 days.

(21) Appl. No.: 10/519,537

(22) PCT Filed: Jun. 30, 2003

(86) PCT No.: PCT/NL03/00483
§ 371 (c)(1), (2), (4) Date: Sep. 20, 2005

(87) PCT Pub. No.: WO2004/003268
PCT Pub. Date: Jan. 8, 2004

(65) Prior Publication Data
US 2006/0099414 A1 May 11, 2006

(30) Foreign Application Priority Data

Jun. 28, 2002 (EP) .................................... 02077579

(51) Int. Cl.
*D02G 3/00* (2006.01)
*D01D 5/06* (2006.01)
*B29C 65/00* (2006.01)
*B01D 33/21* (2006.01)

(52) U.S. Cl. ........ 428/364; 428/373; 264/180; 264/181; 264/184; 264/41; 210/500.23; 210/500.29

(58) Field of Classification Search .................. 428/364, 428/310.5, 398, 372, 376, 379, 400, 401, 428/392, 394, 903; 524/584; 210/510, 500.21; 264/180, 181, 184
See application file for complete search history.

(56) References Cited

U.S. PATENT DOCUMENTS 2,692,185 A * 10/1954 Hooper et. al. ............... 264/182
3,175,339 A * 3/1965 McDowell ....................... 95/142
3,344,177 A * 9/1967 Hensley, Jr. et al. .......... 562/485
(Continued)

FOREIGN PATENT DOCUMENTS
DE 233 385 A 2/1986
JP 63-092712 A 4/1988
(Continued)

OTHER PUBLICATIONS

United State Environemental Protection Agency, Technical Bulletin Zeolite A Versatile Air Pollutant Adsorber, EPA 456/F-98-004, Jul. 1998. pp. 9 and 11.*

*Primary Examiner* — Angela Ortiz
*Assistant Examiner* — Altrev C Sykes
(74) *Attorney, Agent, or Firm* — Buchanan Ingersoll & Rooney PC

(57) ABSTRACT

The invention relates to a method for the preparation of porous polymeric fibres comprising functionalized or active particles. By extruding a mixture of one or more dissolved polymers with particulate material a porous fibre is obtained in which the particulate material is entrapped. Extrusion of the fibre occurs under two-step phase inversion conditions. In particular the porous fibres can be used for the isolation of macromolecules such as peptides, proteins, nucleic acids or other organic compounds from complex reaction mixtures, in particular from fermentation broths. Another application is the immobilization of a catalyst in a reaction mixture.

32 Claims, 4 Drawing Sheets

U.S. PATENT DOCUMENTS

| | | | |
|---|---|---|---|
| 3,493,497 A * | 2/1970 | Pretorius et al. | 210/656 |
| 4,302,509 A * | 11/1981 | Coplan et al. | 428/398 |
| 5,093,197 A * | 3/1992 | Howard et al. | 428/372 |
| 5,238,735 A | 8/1993 | Nagou et al. | |
| 5,258,149 A | 11/1993 | Parham et al. | |
| 5,286,449 A * | 2/1994 | Kuroda et al. | 422/48 |
| 5,744,236 A * | 4/1998 | Rohrbach et al. | 428/372 |
| 5,786,428 A * | 7/1998 | Arnold et al. | 525/333.3 |
| 5,834,107 A * | 11/1998 | Wang et al. | 428/310.5 |
| 6,048,457 A | 4/2000 | Kopaciewicz et al. | |
| 6,454,943 B1 * | 9/2002 | Koenhen | 210/500.21 |
| 6,497,953 B1 * | 12/2002 | Yu et al. | 428/372 |
| 6,500,233 B1 * | 12/2002 | Miller et al. | 95/50 |
| 6,899,834 B2 * | 5/2005 | Boggs et al. | 264/45.1 |
| 2004/0028875 A1 * | 2/2004 | Van Rijn et al. | 428/98 |

FOREIGN PATENT DOCUMENTS

| | | |
|---|---|---|
| JP | 2144133 A | 6/1990 |
| SG | 80604 A1 * | 5/2001 |
| WO | WO 93/12868 A | 7/1993 |
| WO | WO 98/34977 | 8/1998 |
| WO | WO 98/37949 A | 9/1998 |
| WO | WO 98/41312 A | 9/1998 |
| WO | WO 00/02638 | 1/2000 |
| WO | WO 00/22208 | 4/2000 |
| WO | WO 01/02085 A | 1/2001 |

* cited by examiner

FUNCTIONAL POROUS FIBRES

FIELD OF THE INVENTION

The present invention relates to a method for the preparation of porous polymeric fibres comprising functionalised or active particles, in particular comprising particles that are still accessible and active after preparation, and to the porous polymeric fibres thus obtained. Also the invention relates to the use of such fibres as means of purification and/or isolation of a component from a (complex) mixture, like for instance fermentation broths or as catalyst in reaction mixtures. For such use preferably the porous polymeric fibres are comprised in modules such as described hereinbelow.

BACKGROUND OF THE INVENTION

Porous polymeric matrices comprising particles have been described before.

For instance in U.S. Pat. No. 6,048,457 cast porous polysulfone membrane structures comprising sorptive particles such as active carbon, (fumed or derivatised) silica or (functionalised) polystyrenedivinylbenzene beads are described. It concerns cast-in-place structures confined in pipette tips for small scale sample preparation.

Another example is U.S. Pat. No. 5,258,149 in which a hollow fibre membrane comprising polysulfone polymer and silica is described. It is stated that silica acts as a pore former and viscosifier in membrane formation and that fibres with silica are not microporous until the bulk of the silica is removed by treatment with base. The hollow fibre membrane is immobilised by heat treatment under pressure in the presence of polyacrylic acid. The polyacrylic acid binds to the fibre walls and acts as an affinity agent for low density lipoprotein cholesterol complex (LDL-C).

In U.S. Pat. No. 5,238,735 the preparation of a microporous polyolefin hollow fibre comprising synthetic resin particles is described by extruding a mixture of (co) polyolefin(s), synthetic resin particles and plasticiser, from a melt at a temperature of 230° C., into a strand which was cut into pellets. The resulting pellets were extruded from the melt at a temperature of 215° C. through a hollow fibre producing nozzle. In order to introduce the desired porosity the unstretched hollow fibre is monoaxially stretched by a roll-stretching method resulting in a molecularly oriented microporous hollow fibre.

Also in WO 00/02638 a porous polymeric matrix comprising substantially immobilised material is described. Such a flexible sheet membrane (flat, pleated or rippled) has a selectively permeable skin on the outer surface. In particular the preparation of a membrane by flow casting a slurry-like blend of polyurethane and activated charcoal onto a polyester support is described. It is mentioned that the blend can also be extruded onto a support. Further it is also noted that the membrane can be made without an integral support, for instance by applying the blend to a drum and thereafter peeling the membrane off the surface of the drum. In passing it is noted that also other configurations than flat sheet membranes can be formed such as fibres, rods and tubes. However, besides the embodiment of flow casting a membrane onto a support none of the other suggestions are enabling disclosed.

In WO 98/34977 a porous composite product formed from at least one water-insoluble polymer, at least one water-soluble polymer and at least 20% of at least one filler material, in particular active carbon, is described. The product is obtained by a melt extrusion process, using an extruder. The porosity in the product is introduced by eliminating the soluble polymer from the extruded product. It is stated the polymeric material is non-fibrous and rather concerns a film of porous composite products.

Thus, in the art methods are known to prepare porous polymeric material comprising particulate material in one step from an appropriate mixture of starting components. Such a material is prepared by a casting process and either is limited in its three dimensional size by the housing it is cast into or is in the form of a sheet. Such casting processes are not suitable for the preparation of fibres.

In order to prepare porous polymeric fibres comprising particulate material an additional process step is required to introduce the desired porosity. After the step of preparing the fibre comprising particulate material either particulate material is removed form the non-porous fibre or the non-porous fibre is stretched resulting in porous fibres. Only in the latter case a microporous fibre comprising particles having a certain (sorptive) function is obtained.

Disadvantages of the known porous polymeric fibre preparation processes are that they involve additional process steps after the formation of the fibre to come to a final product. It is desirable to have a more efficient preparation process. Depending on the actual process steps that need to be taken to come to the final product suitable starting materials have to be selected with properties that can sustain the conditions of the additional process steps. Obviously such a requirement puts limitations on the polymeric material that can be used. Furthermore it puts limitations on the type of particulate material that can be comprised in the polymeric matrix. A high degree of particle loading will reduce the mechanical strength of the fibre and therefore restrict the stretching procedure. The degree of loading will be limited by the force required to reach sufficient stretching of the matrix material. By stretching of the particle comprising material the particulate material can drop out of the porous structure to be formed. In processes which involve melt extrusion only particulate material that can sustain temperatures required to melt the matrix polymer can be applied. It is not uncommon that these temperatures are well above 200° C.

DD A 233,385 discloses a method for the preparation of porous fibres, comprising a one-step phase inversion or so-called wet-spinning process. Immediately after extrusion the fibre enters a coagulation bath. Particles are applied to maintain porosity during drying at elevated temperatures; the accessibility and functionality of the particles are less critical therein. It is stated that the properties and behaviour of the end-product are essentially determined by the chemical structure of the polymer used.

Drawback of a method according to DD A 233,385 is that direct spinning in a coagulation bath with less than 60 wt. % solvent results in rather dense exterior surfaces and limited particle accessibility. However, an increase in the amount of solvent results in difficulties of controlling the spinning process; due to delayed demixing of the nascent fibre solidification takes too long.

SUMMARY OF THE INVENTION

It is an object of the invention to provide a porous fibre comprising particulate material having a certain functionality by a process, which can be operated at room temperature or reigned temperatures and does not require additional process steps after the formation of the fibre.

A further object is to provide a method allowing the use of a variety of functional particles that can be taken up in the polymeric matrix or support structure. Multiple types of particles with different functionalities or particles with more than one functionality may be used.

Said functional particles should be accessible and maintain their functionality once incorporated inside the matrix (support structure) of the porous fibre.

Surprisingly it has been found that the objects of the invention are met by a method in which a solution of one or more polymers is mixed with particulate material. By extruding the resulting mixture a porous fibre can be obtained in which the particulate material is entrapped. Optionally additives and/or non-solvents may be added to the polymer solution. Extrusion of the fibre occurs under phase inversion conditions.

Thus, according to the invention a method is provided for the preparation of a polymeric matrix having particulate material entrapped in said matrix in which the polymeric matrix is porous and the particles are well accessible and maintain their functionality after preparation, said method comprising providing a mixture of dissolved polymeric material and particulate material and extruding said mixture into a fibre and solidify said fibre by a two-step phase inversion process.

DETAILED DESCRIPTION OF THE INVENTION

Figure 1:
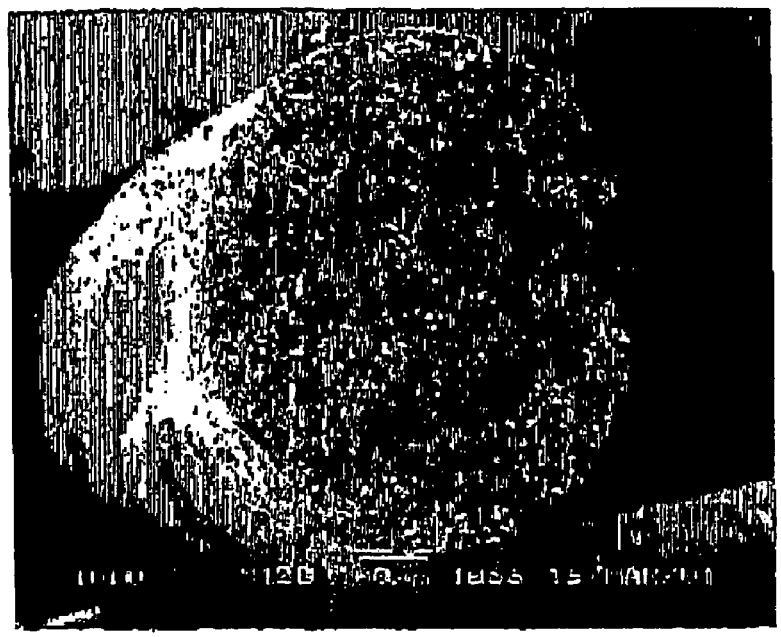
FIG. 1 is a scanning electron micrograph (SEM) of a porous solid fibre prepared according to example 1.
Figure 2:
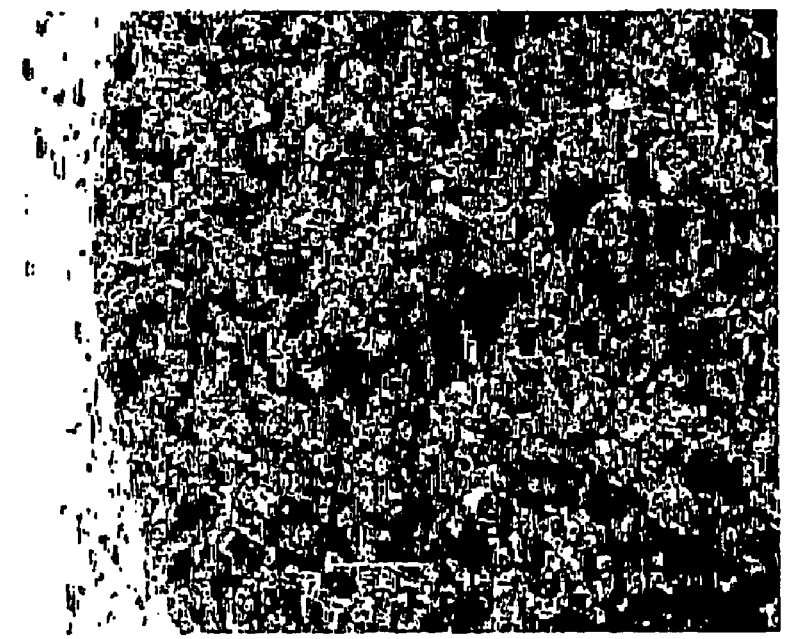
FIGS. 2 and 3 arm magnifications of FIG. 1.
Figure 3:
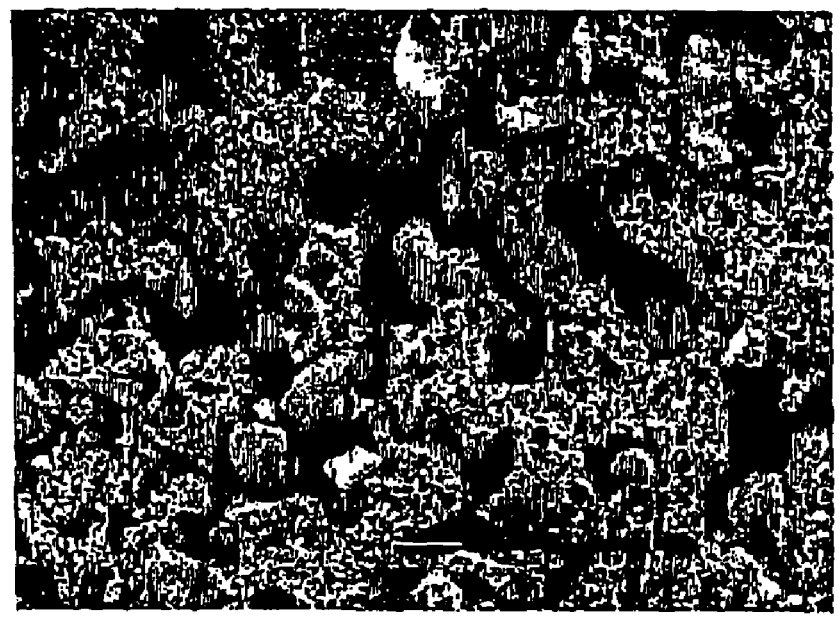
Figure 4:
FIG. 4 is a scanning electron micrograph (SEM) of a porous hollow fibre prepared according to example 2.

A method has been found for the preparation of a porous polymeric fibre having particulate material in said fibre. Advantageously in the step in which the fibre is formed the porosity in the fibre is introduced simultaneously and thus the necessity of additional pore forming treatments is no longer present.

An additional advantage of the method of the invention is that it does not influence the integrity of the particulate material during the extrusion step. The method offers the possibility to entrap particles having a variety of functionalities in a polymeric matrix. Heat sensitive particles that cannot be melt-extruded because of the elevated temperatures required to melt the matrix polymer can be incorporated into a porous matrix by the phase inversion process without danger of damaging the particle. The fibres can be processed under mild conditions.

Extrusion of the fibre occurs under phase inversion conditions. Phase inversion, or phase separation, can be induced by: the change of temperature of the homogeneous solution (thermal phase separation), the evaporation of solvent from a polymer solution that contains a non volatile non-solvent (evaporation induced phase separation), the penetration of a non-solvent vapor (vapor induced phase separation), or immersion of the homogeneous polymer solution in a non-solvent bath (immersion induced phase separation).

In general phase inversion extrusion processes require polymer solutions in which the concentration of polymer is more than 12% by weight. Unexpectedly the presence of particulate material allows the use of polymer solutions of lower concentration. In particular it allows the use of polymer concentrations of less 12% by weight, more particularly of less than 10% by weight.

By the method of the invention it is possible to establish particle loaden matrices of infinite length. Obviously it is to be understood that instead of a particle loaden matrix of infinite length also matrices of very short length can be produced by the same technique. Either the infinite matrix structure is cut or crushed into small pieces after the structure is solidified, or the polymer solution containing the particles is extruded through an extruder such as a spinneret at short intervals or by other means that causes droplets leaving the extruder instead of a continuous fibre.

The term fibre used herein includes hollow and solid fibres. Depending on the type of application a suitable form of the fibre; either hollow or solid, is selected.

Also depending on the desired objectives and properties of the resulting fibres a person skilled in the art will appreciate that many different particles can be used. For instance when applied as a means for detoxification or purification by removing toxic or undesired (small) organic compounds absorptive particulate material may be used such as for instance activated carbon.

In a preferred embodiment of invention however, the porous fibres are applied to isolate desired molecules. In particular such an application concerns the isolation of macromolecules such as peptides, proteins, nucleic acid or other organic compounds. In such a case the use of adsorptive particles is preferred. Most suitable particles will have, in combination with the porous matrix morphology, rapid adsorption kinetics, a capacity and selectivity commensurate with the application and allows for desorption of the molecule with an appropriate agent. The affinity of suitable adsorptive particles for specific molecules can be defined in terms of hydrophobic, hydrophilic or charged functionalities, in particular ion exchange functionalities, molecular (imprinted) recognition, epitope recognition, isomer selective or other specific interactions. In an embodiment suitable adsorptive particulate material is hydrophobic in nature.

In further embodiments the particulate material is functionalized for size exclusion or for the separation of optically active compounds or the separation of isomers or can be used in reversed phase chromatography. Separation of optically active compounds or the separation of isomers may be based on selective affinity.

In another embodiment the particles are functionalised in order to serve as a component in a reaction mixture to promote reactivity in particular as catalyst. Also it may be desirable to combine adsorption and catalysis. In particular the catalyst may be a biocatalyst.

Suitable adsorptive particles will be apparent to those skilled in the art and include cation exchange resins, union exchange resins, silica type particles, for instance unmodified or derivatised with $C_2$, $C_4$, $C_6$, $C_8$ or $C_{18}$ or ion exchange functionalities, zeolites, ceramic particles, such as $TiO_2$, $Al_2O_3$, and the like, magnetic colloidal particles, porous or non-porous polymeric particles, such as porous polystyrene or styrene-divinylbenzene type particles either unmodified or derivatised with for instance sulphonic acids, quaternary amines and the like, molecular imprinted particles and homogeneous) catalyst particles.

In a further embodiment the functional particle inside the porous matrix may be altered in its function by a subsequent functionalisation. Ion-exchange particles may for example adsorb a protein which remains on the particle by a subsequent crosslinking reaction. The protein modified ion-exchange (IEX) particle now has a function different from its original adsorption function. For example, the protein modified IEX particle may have now different adsorptive functionality or different enantiomer separation. Another example is for instance the immobilisation of a (homogeneous) catalyst on the functional particle inside the porous matrix.

The term particulate material as used herein is intended to encompass particles having regular, in particular spherical or irregular shapes, as well as shards, fibres and powders, including metal powders, plastic powders for instance powdered polystyrene, normal phase silica, fumed silica and activated carbon.

Particles with an average particle (diameter) up to 100 μm may be used. It is preferred the average particle size is less than 50 μm and is preferably in the range of 0.1 to 30 μm, preferably smaller than 20 μm.

The polymeric material may be a polymer including elastomers, a copolymer, mixture of polymers, mixture of copolymers or a mixture of polymers and copolymers. Examples of polymeric materials suitable for use in the preparation of porous fibres according to the method of the invention include polysulphone (PSF), polyethersulphone (PES), polyamide (PA), polyetherimide (PEI), polyimide (PI), polyethylene-co-vinylalcohol (EVAL), polyethylene-vinylacetate (EVAC), cellulose acetate (CA), cellulose triacetate (CTA), polyvinylidenefluoride (PVDF), polyvinylchloride (PVC) polyacrylonitrile (PAN), polyurethane (PUR) polyether ether ketone (PEEK) polyacrylicacid (PAA). However the invention is not limited to those polymeric materials and other suitable materials may be apparent to the skilled person. Also polymers having modifications, chemically and/or physically, may be used such as for instance sulfonated polymers. Also mixtures of two or more polymers may be used. In general it is advantageous to use polymers that are compatible with components found in food products. Preferably such polymers demonstrates a low interaction with food components, this to prevent non-selective interactions, with components out of the feed stream.

Preferred polymeric materials are polyethersulphone, polysulfone, polyethylene-co-vinylalcohol, polyvinylidenefluoride an cellulose acetate.

In the method of the invention the polymeric material should be dissolved in a suitable solvent. The type of solvent depends on the choice of the polymer. In view of the phase inversion process preferably solvent are used that are well miscible with water. One or more solvents can be used together even in combination with nonsolvents. Suitable solvents include, but are not limited to N-methyl-pyrrolidone (NMP), dimethyl acetamide (DMAc), dimethylformamide (DMF), dimethylsulfoxide (DMSO), formamide (FA), tetrahydrofurane (THF), ε-caprolactam, butyrolactone, in particular 4-butyrolactone, sulfolane, cyclohexanons and triethylphosphate. Preferred solvents are NMP, DMAc, DMF, DMSO, THF, ε-caprolactam and 4-butyrolactone.

Water is the preferred coagulation medium. Other examples of possible coagulation media and non-solvents are methanol, ethanol, propanol, butanol, ethylene glycol, aceton, methyl ethyl ketone.

Intimately mixing the solvents the polymeric matrix material and the particulate material provides the basic mixture that is to be extruded.

In order to obtain the desired porosity in the fibres mixtures of non-solvents and solvents in combination with variation in physical process parameters like temperature, production rate, humidity, air gap length, stretching and take up speed are used. Also for various reasons additives may be applied such as for instance to influence viscosity of the polymer solution, as pore former, as pore connectivity enhancer, to reduce or prevent macro-void formation and/or to introduce hydrophilicity. Possible additives include, but are not limited to polyvinylpyrrolidone (PVP), polyethylene glycol (PEG), polyethyleneoxide (PEO), dextran, glycerol, diethylene glycol, (higher) alcohols such as octanol, carboxylic acids or organic acids, such as oxalic acid, maleic acid, tartaric acid, fumaric acid, salts, such as LiCl and $CaCl_2$. It is within the competence of the skilled person to assess and apply suitable (mixtures) of (non-)solvents, additives and process conditions to produce a fibre with desired properties.

For the production of fibres, either hollow, solid or solid supported, generally known extruders may be used. For instance by using a double-walled cylindrical (tube-in-orifice) spinneret and applying a bore liquid a hollow fibre is obtained. Not applying a bore liquid results in the formation of a solid fibre. By spinning a thread or net with the polymer a composite fibre can be obtained. Extrusion into a water bath results in solidification of the porous fibre having particulate material entrapped.

The matrix polymer concentration in the polymer solution is between 0.5 and 50% by weight. The suitable amount of particles in the mixture that is to be extruded depends on type of polymer and the concentration of the polymer that is used. In general the amount of particles in the mixture that is to be extruded may vary between 1 and 95% by weight. Thus the mixture that is extruded comprises 0.5% to 50% by weight polymeric material and 1% to 95% by weight of particulate material, the remainder being solvent. Additives and/or non-solvent can partly replace the solvent and can vary between 0.01 and 50% by weight.

In an embodiment the matrix polymer concentration in the polymer solution is between 3 and 50% by weight and preferentially between 5-35% by weight. Preferably the matrix polymer concentration is less than 12%, more preferably less than 10% by weight. The preferred concentration depends on the specific polymer or polymers that are used, in combination with the specific particulate material and the desired amount of particles in the fibre that is to be obtained.

In an embodiment the amount of particles in the mixture that is to be extruded varies between 1 and 60% by weight. Preferably the amount of particles in the mixture that is to be extruded is more than 5% by weight, being preferentially between 10 and 60% by weight. Thus the mixture that is extruded comprises 3% to 50% by weight polymeric material and 1% to 60% by weight of particulate material, the remainder being solvent. Additives and/or nonsolvent can partly replace the solvent and can vary between 0.01 and 50% by weight.

Figure 7:
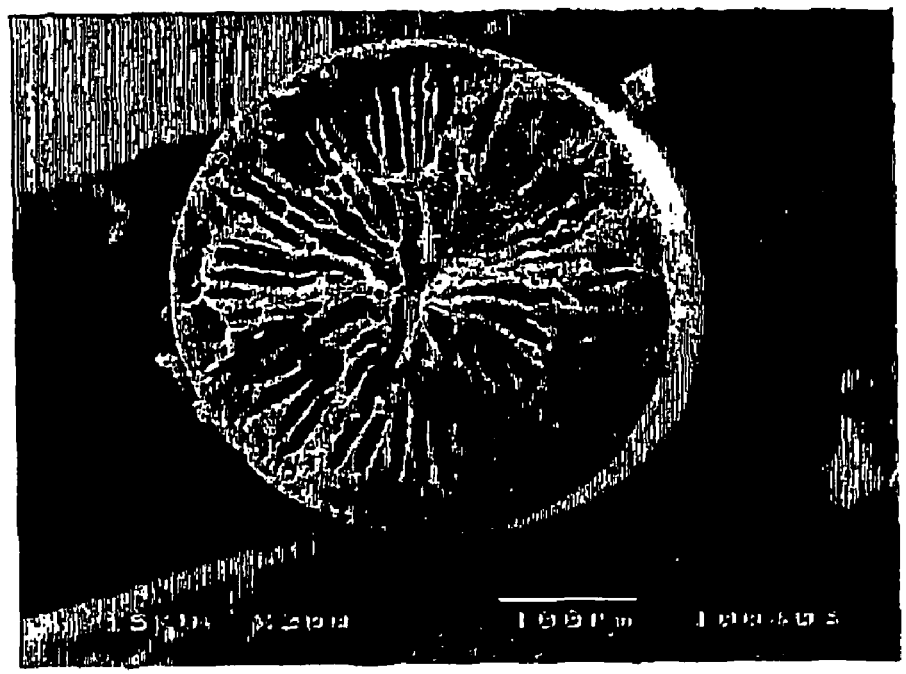
FIG. 7 shows a SEM picture of a PES/CER fibre with a particle content of 10% by weight. Macrovoids are clearly visible.
Figure 8:
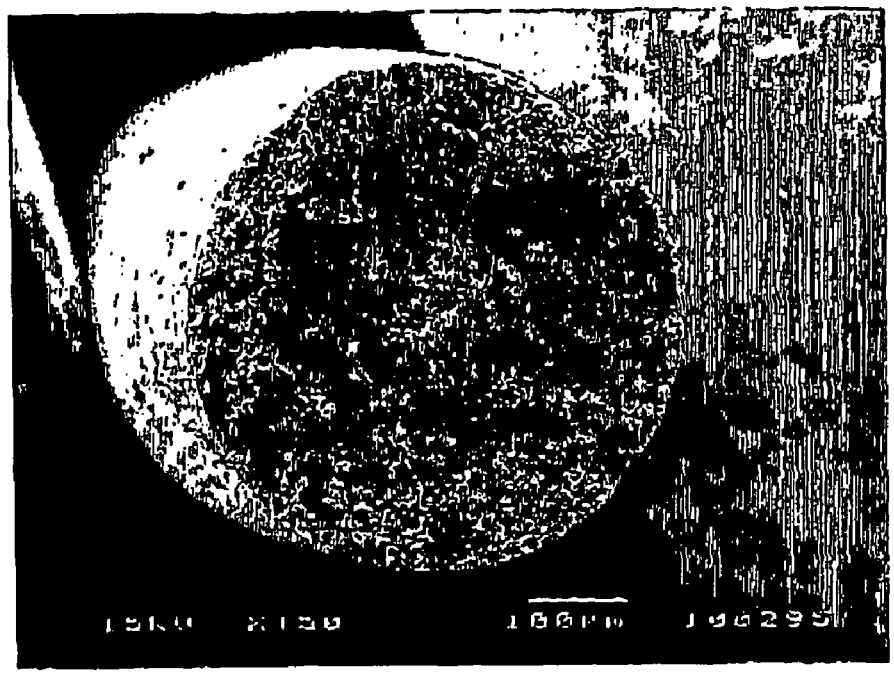
FIG. 8 shows a SEM picture of a PES/CER fibre with a particle content of 75% by weight. The fibre is free of macrovoids.

Furthermore, unexpectedly, it has been found that the size of the particle, the functionality as well as the amount of particles in the polymer solution have a distinct influence on the ultimate pore structure of the matrix. The smaller the particles the more spongy the matrix structure becomes. For instance it was observed that going from 90 μm particles to 20 μm the structure changes form a macrovoid containing structure to a completely macrovoid free structure. Furthermore, the accessibility of the particles is significantly improved when the particle content increases. FIGS. 7 and 8 show the change in porosity going from a fibre with 10% by weight of particulate material to a fibre with 75% by weight of particulate material.

In general it may be assumed that it is desired to have a polymeric matrix with as many particles as possible that are well accessible. However, it may also be assumed there is a balance between particle load and accessibility, depending on a particular application of the polymeric matrix. It may even be advantageous to use a polymeric matrix having macrovoids, which may be beneficial in view of convective transport and diffusional resistance in the polymeric matrix.

Thus in an aspect of the invention a method is provided for controlling porosity of a polymeric matrix having particulate material entrapped in said matrix by varying the size of the particulate material. In yet a further aspect a method is provided for controlling porosity of a polymeric matrix having particulate material entrapped in said matrix by varying the content of the particulate material. In yet a further aspect a method is provided for controlling porosity in a polymeric matrix having particulate material entrapped in said matrix by varying the functionality of the particulate material. Varying functionality means chemical groups in or on or of a particle.

The fibre that is prepared according to the method of the invention comprises 5-95% by weight of polymeric material and 5-95% by weight of particulate material, preferably 60-95% by weight of particulate material. Even at particle weight percentages of 75 and higher fibres have been obtained with sufficient mechanical strengths. In an embodiment the fibre that is prepared according to the method of the invention comprises 20-70% by weight of polymeric material and 30-80% by weight of particulate material, preferably 60-70% by weight of particulate material.

To produce fibres with desired porous properties a two-step phase inversion process is used. Prior to entering a coagulation bath the exterior of the nascent fibre is in contact with a chosen media resulting in a change in composition of the exterior layer. This is considered as the first step of the phase separation process. When the fibre enters the coagulation bath the nascent fibre will further phase separate and the structure will be arrested. This is considered as the second step of the phase separation. In the first step the pore size and porosity of the outer wall of the fibre can be adjusted.

To influence the environment of the exterior of the polymer solution leaving the die of the extruder, in a two stop phase inversion process in particular extrusion by means of a spinneret is used. Preferably a set-up is such in which a spinneret is used that allows for the controlled flow of a liquid, a vapor or a gas as an exterior medium of the fibre. Advantageously the two-step phase inversion process involves the use of a so-called triple layer spinneret as described in WO 93/12868. The use of a triple layer spinneret is synonym for a two-step phase inversion fiber formation process. A triple layer spinneret allows for the controlled flow of a liquid, a vapor or a gas an exterior medium along the fibre. For hollow fibers a bore liquid is applied through the needle of the triple layer spinneret, which influences the inner surface structure. For the preparation of solid fibers the needle has no function and could even be missed.

The choice of the composition of the exterior medium in the triple layer spinneret and the contact time prior to entering the coagulation bath determine whether the exterior fibre surface becomes dense or porous. When the exterior is in contact with air of moderate humidity the exterior surface of the fibre turns out dense. To profit of optimal accessibility of the entrapped particles a suitable medium should be flown along the exterior of the fibre during spinning. Preferably the exterior medium is a liquid mixture of solvent and nonsolvent for the polymer. Preferably the nonsolvent is water. Alternatively it is possible to apply a gas stream comprising a nonsolvent for the polymer. In this case preferably the nonsolvent is water vapor. A skilled person can easily determine the desired amount of water vapor in the gas stream to produce a first phase inversion effect.

A two-step phase separation process, where the nascent fibre contacts two different media consecutively, and which both influence the nascent fibre composition by interchange of solvent and nonsolvent, bypasses the type of difficulties that relate to a one-step phase inversion process as disclosed in DD A 233,385, wherein the contact time with the first medium is short and the second medium is a strong coagualant for the nascent fibre composition. The two-step phase inversion process that is applied according to the method of the present invention ensures that the particles in the porous matrix are well accessible and maintain their functionality after preparation.

A simple tube-in-orifice spinneret can also be used, but offers less flexibility in altering the shell surface. Of course when solid fibres are produced the inner needle is no longer required and the triple layer spinneret is degraded to a tube-in-orifice spinneret, where the polymer solution is spun through the needle and the first coagulant through the orifice. In that case the dimensions of the tube and the orifice have to be adjusted accordingly.

For additional enforcement of the fibre one or more thread wires, yarns or the like of any material can be co-extruded with the fibre and being entrapped in the core of the solid fibre or in the wall of the hollow fibre as essentially is described in WO 01/02095.

Typically the size of the pores in the fibre are not greater than 20 µm. Although the pore size is dependent on the application it should not be larger than the particle size to avoid particle loss during processing.

The optimum diameter of the fibre depends on the diffusion coefficient of the target particles, length of the adsorber and flow conditions. Typical fibre diameters are between 10 µm or 20 µm and 15 mm where as is most cases it is beneficial to use fibres with diameters between 0.3 or 0.5 and 3 mm.

The thus produced porous fibre may undergo post treatment such as for instance heat treatment or further functionalisation steps to activate the particle or to fix the porous structure of the fibre or to reduce the size of the pores of the porous fibre. Depending on polymer and particles used, the skilled person will be able to determine a suitable temperature or temperature range to apply in the heat treatment.

The invention further relates to a fibre obtainable by the method according to the invention.

The fibres prepared according to the method of the invention can be used as such, however, in another embodiment of the invention the fibres are comprised in a module. Suitably such a module comprises spirally wound fiber mats packed inside a housing, a bundle of fibers packed longitudinally inside a housing, transverse flow fiber configuration inside a housing, fibers wounded as a spool in parallel or cross-over mode inside a housing or any other orderly or disorderly fiber packing configuration inside a housing. Also other bodies comprising fibres, optionally in a finely divided form, prepared according to the method of the invention are within the scope of the invention. Such bodies include for instance columns for chromatography.

The porous fibres and modules of porous fibres of the invention have a wide variety of applications, depending upon the particle selection. They may be used for the adsorption and/or purification of compounds from a reaction mixture or in fact from any compound mixture. For example, applications include peptide and protein isolation, immobilised ligands for affinity based separations, chromatography, immobilised catalysts and enzymes for reactions, release and product protection etc. Those skilled in the art will be able to choose the appropriate particles and particle functionalisation in combination with appropriate polymeric material and optionally additives depending upon the desired application. Also a mixture of particles may be used.

A particular use of interest is the isolation of desired proteins from fermentation broths, tissue broths, plant broths or cell broths in general, catalytic and enzymatic reactions, detoxification, product protection and release systems.

Example 1

Solid Fibre Polyethylene-Vinyl-Alcohol/Cation Exchange Resin Structure

A polyethylene-vinyl-alcohol (EVAL with 44% ethylene content) solid fiber was produced by dissolving 7 wt. % EVAL and 12 wt. % cation-exchange resin (CER) (Lewatit CNP 80 WS (Bayer), total ion-exchange capacity: 4.3 eq/l) and 7 wt. % octanol in dimethylsulfoxide (DMSO). The resin particles were smaller than 20 μm. The obtained dispersion was extruded through a tube-in-orifice spinneret (OD=2.4 and ID=1.65 mm) into a water bath (20° C.), where phase separation occurred. There was no bore liquid used for the production of solid fibre. This way a porous solid fibre was obtained with a particle load of 60 wt. % CER, with 80% of the immobilised particles being active for protein (BSA) adsorption. A BSA adsorption of 80 mg/g fibre has been obtained.

Example 2

Hollow Fibre Polysulfone/Cation Exchange Resin Structure

A polysulfone hollow fibre was produced by dissolving 30 wt. % polysulfone (UDEL 3500) and mixing it with 30 wt. % of the styrene-divinylbenzene type cation-exchange resin (CER) (Amberlite IR-120, total ion-exchange capacity: 4,4 meq/g-dry resin) in N-Methylpyrrolidone (NMP). The resin particles were smaller than 30 μm. This dispersion was extruded through a tube-in-orifice spinneret (OD=2.1 and ID=1.0 mm) into a water bath (16-18° C.), where phase separation occurred. The bore liquid consisted of 60% NMP and 40% water. The spinning rate was 0.35 m/min. This way a porous hollow fibre was obtained with a particle load of 50 wt. % CER, with 88% of the immobilised particles being accessible for salt ions.

The produced hollow fibre without a post treatment shows a NaOH flux of 7.9 mol·hr·m$^2$ and a Na$_2$SO$_4$ flux of 2.4 mol·hr·m$^2$. This results in a rather low selectivity of 3.3. It appears that a heat treatment of the produced fibres just above the glass transition temperature of the matrix polymer influences the fibres' properties considerably. A heat treatment of 10 minutes at 200° C. reduced the fluxes of NaOH and Na$_2$SO$_4$ to values of 1 and 0.01 mol·hr·m$^2$, respectively. The NaOH/Na$_2$SO$_4$ selectivity increased form 3.3 to 102.

Example 3

Solid Fibre Polyethylene-Vinyl-Alcohol/BSA-Modified Cation Exchange Resin Structure A polyethylene-vinyl-alcohol (EVAL with 44% ethylene content) solid fibre was produced by dissolving 7 wt. % EVAL and 12 wt. % cation-exchange resin (CER) (Lewatit CNP 80 WS (Bayer), total ion-exchange capacity: 43 eq/l) and 7 wt. % octanol in dimethylsulfoxide (DMSO). The resin particles were smaller than 20 μm. The obtained dispersion was extruded through a tube-in-orifice spinneret (OD=2.4 and ID=1.65 mm) into a water bath (20° C.), where phase separation occurred. There was no bore liquid used for the production of solid fibre. This way a porous solid fibre was obtained with a particle load of 60 wt. % CER. The functional porous fibre was used for adsorption of bovine serum albumin (BSA) in a batch experiment. The functional porous fibres have an adsorption capacity of 165 mg BSA/g fibre. The BSA-modified functional porous fibre was consecutively treated with a glutaraldehyde (GA) solution to chemically attach the protein into the porous matrix. The resulting solid fibre of polyethylene-vinyl-alcohol/BSA-modified cation exchange resin structure adsorbs bilirubin. It therefore has also the potential to adsorb other substances such as tryptophan, barbiturates or antidepressant.

Example 4

Solid Fibre Polyethylene-Vinyl-Alcohol/Polyethyleneimine-Modified Zirconia Particles Selective for Endotoxins A polyethylene-vinyl-alcohol (EVAL with 44% ethylene content) solid fibre was produced by dissolving 7 wt. % EVAL and 12 wt. % porous zirconia microspheres and 7 wt. % octanol in Dimethylsulfoxide (DMSO). The zirconia particles were smaller than 20 μm and can be either obtained commercially or synthesized tailored to the desired properties by polymerization-induced colloid aggregation. The obtained dispersion was extruded through a tube-in-orifice spinneret (OD=2.4 and ID=1.65 mm) into a water bath (20° C.), where phase separation occurred. There was no bore liquid used for the production of solid fibre. This way a porous solid fibre was obtained with a particle load of 63 wt. % zirconia. The fibre thus obtained was further treated to immobilize polyethyleneimine (PEI) onto the zirconia particles by coating it with a 2 wt. % PEI solution in methanol. Crosslinking of the PEI by agents such as 1,2-bis-(2-iodoethoxy)ethane or 1,10-diiododecane can influence the hydropholicity of the quaternized PEI. Such functional porous fibres of polyethylene-vinyl-alcohol/polyethyleneimine-modified zirconia particles adsorb selectively endotoxins over proteins.

Example 5

Solid Fibre Polyethersulfone Cation Exchange Resin Structure

Figure 5:
FIG. 5 shows a SEM picture of the exterior surface of a solid PES/CER fibre prepared with a NMP/water (70/30 wt. %) mixture as first coagulant according to example 5.
Figure 6:
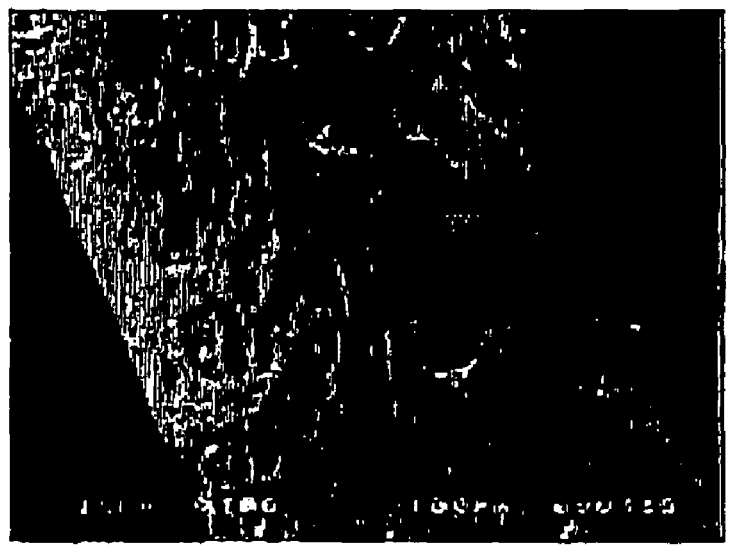
FIG. 6 shows a SEM picture of the exterior surface of a solid PES/CER fibre prepared with a NMP/water (90/10 wt. %) mixture as first coagulant according to example 5.

A polyethersulfone (PES) solid fibre was produced by dissolving 13.8 wt. % PES and 13.8 wt. % cation-exchange resin (CER) (Lewatit CNP 80 WS (Bayer), total ion-exchange capacity: 4.3 eq/l), 33.6 wt. % polyethylene glycol (PEG 400) and 5.2 wt. % water in N-Methylpyrrolidone (NMP). The resin particles were smaller than 20 μm. The obtained dispersion was extruded through a triple layer spinneret (OD=2.4 and ID=1.65 mm) into a water bath (20° C.), where phase separation occurred. There was no bore liquid used for the production of the solid fibre. At the exterior of the nascent fibre mixtures of NMP and water (first coagulant) were flown. The contact time with the first coagulant was less than 1 second. This way a porous solid fibre was obtained with a particle load of 50 wt. % CER. Scanning Electron Microscopy (SEM) pictures show clearly that the exterior surface is much denser when a first coagulant is used of 70 wt. % NMP and 30 wt. % water compared to a mixture of 90 wt. % NMP and 10 wt. % water, see FIGS. 5 and 6.

Example 6

Influence of Particle Content

To demonstrate the influence of particle content on the porosity of polymeric matrix fibres according to example 5 were prepared with varying particle contents. FIG. 7 shows a fibre with a particle content of 10% by weight in which clearly macrovoids are visible. FIG. 8 shows a fibre with a particle content of 75% by weight in which is free of macrovoids.

The invention claimed is:

1. Method for the preparation of a polymeric support matrix having particulate material entrapped in said support matrix in which the polymeric support matrix is porous and the particles are well accessible and maintain their functionality after preparation, said method comprising providing a mixture of polymeric material and particulate material in a solvent for the polymeric material and extruding said mixture into a fibre and solidifying said fibre by a two-step phase inversion process,
wherein the two-step phase inversion process comprises:
(i) utilizing a spinneret to allow a controlled flow of a liquid mixture comprising a solvent and a non-solvent for said polymeric material, along an exterior medium of the nascent fibre, resulting in a first phase separation of the exterior of the nascent fiber; and
(ii) entering of said fiber into a coagulation bath, resulting in further phase separation and arrest of the structure of said fiber,
to obtain a hollow or solid fiber containing about 60-95 wt % of particulate material.

2. Method according to claim 1 in which the mixture that is extruded comprises 0.5% to 50% by weight polymeric material and 1% to 95% by weight particulate material, the remainder being solvent.

3. Method according to claim 1 in which the solvent is selected from the group consisting of N-methyl-pyrrolidone (NMP), dimethyl acetamide (DMAc), dimethylformamide (DMF), dimethylsulfoxide (DMSO), tetrahydrofurane (THF), $\epsilon$-caprolactam and 4-butyrolactone.

4. Method according to claim 3 in which the solvent in the mixture of polymeric material and particulate material is replaced by 0.01-50% by weight of one or more additives and/or non-solvents.

5. Method according to claim 4 in which the additives are selected from the group consisting of octanol, polyvinylpyrrolidone (PVP), polyethylene glycol (PEG), and glycerol.

6. Method according to claim 1 in which the fibre comprises about 60-70% by weight of particulate material.

7. Method according to claim 1 in which the nonsolvent is water or water vapor.

8. Method according to claim 1 in which the spinneret is a triple layer spinneret.

9. Method according to claim 1 in which the polymeric material is selected from the group consisting of polyethersulphone, polysulfone, polyethylene-co-vinylalcohol, polyvinylidenefluoride and cellulose acetate.

10. Method according to claim 1 in which the particulate material in the porous matrix is altered in its function by a subsequent functionalisation.

11. Method according to claim 1 in which the particulate material is adsorptive particulate material.

12. Method according to claim 1 in which the adsorptive particulate material is an ion exchange resin.

13. Method according to claim 12 in which the adsorptive particulate material is hydrophobic in nature.

14. Method according to claim 1 in which the particulate material is used for size exclusion.

15. Method according to claim 1 in which the particulate material is used for separation of isomeric compounds.

16. Method according to claim 1 in which the particulate material is used for separation of optically active compounds.

17. Method according to claim 1 in which the particulate material is used in reversed phase chromatography.

18. Method according to claim 1 in which the particulate material is functionalised, or is subsequently functionalised, with a catalyst or a biocatalyst.

19. Method according to claim 1 in which the particulate material is active carbon.

20. Method according to claim 1 in which for mechanical enforcement a thread, wire, or yarn is co-extruded with the fibre.

21. Method according to claim 1 which further comprises heat treatment.

22. Method for controlling porosity of a polymeric matrix having particulate material entrapped in said matrix by varying the size of the particulate material in the method according to claim 1.

23. Method for controlling porosity of a polymeric matrix having particulate material entrapped in said matrix by varying the content by weight of the particulate material in the polymeric matrix in the method according to claim 1.

24. Method for controlling porosity of a polymeric matrix having particulate material entrapped in said matrix by varying the functionality of the particulate material in the method according to claim 1.

25. Fibre obtained by the method according to claim 1.

26. Module comprising fibre according to claim 25, said module comprising a spirally wound fiber mat packed inside a housing, a bundle of fibers packed longitudinally inside, a housing, a transverse flow fiber configuration inside a housing, fibre wounded as a spool in parallel or cross-over mode inside a housing or an orderly or disorderly fibre packing configuration inside a housing.

27. Body comprising a fibre, optionally in a finely divided form, according to claim 25.

28. A method for the adsorption and/or purification of compounds from a mixture of compounds or a reaction mixture comprising utilizing a fiber according to claim 25.

29. A method for the immobilization of a catalyst in a reaction mixture comprising utilizing a fiber according to claim 25.

30. A method for the immobilization of a chemical or biological compound comprising utilizing a fiber according to claim 25.

31. The method according to claim 28, wherein the mixture of compounds or the reaction mixture is a fermentation broth, a tissue broth, a plant broth or a cell broth.

32. The method according to claim 1, wherein there is no additional step after (ii).

* * * * *